United States Patent [19]

Franssen et al.

[11] Patent Number: 5,826,585

[45] Date of Patent: Oct. 27, 1998

[54] METHOD FOR DIAGNOSIS OF INCONTINENCE OF CORTICOCEREBRAL ORIGIN BY NEUROLOGIC EXAMINATION

[76] Inventors: Emil H. Franssen, 595 Main St., #1102, New York, N.Y. 10044; Barry Reisberg, 20 Waterside Plz., #7K, New York, N.Y. 10010

[21] Appl. No.: 653,130

[22] Filed: May 24, 1996

[51] Int. Cl.$^6$ ................................................... A61B 19/00
[52] U.S. Cl. ................................................ 128/898; 600/587
[58] Field of Search ................................ 128/898, 630, 128/DIG. 25, 774, 731, 733; 600/587

[56] References Cited

U.S. PATENT DOCUMENTS

| | | | |
|---|---|---|---|
| 4,669,478 | 6/1987 | Robertson | 128/630 |
| 5,150,716 | 9/1992 | Franssen et al. | 128/774 |

OTHER PUBLICATIONS

Souren et al. "Contractures and Loss of Function in Patients with Alzheimer's Disease." J Am Geriatr 43(6):650–5 June. 1995.

*Primary Examiner*—Mickey Yu
*Assistant Examiner*—Kelly O'Hara
*Attorney, Agent, or Firm*—Gottlieb, Rackman & Reisman, P.C.

[57] ABSTRACT

Neurologic measures, namely the hand grasp reflex (syn. palmar grasp reflex), the foot grasp reflex (syn. plantar grasp reflex), the tactile sucking reflex, and the extensor plantar reflex, and, additionally, when a specific magnitude of activity and cut-off score is applied, alone and especially in certain combinations, are used to diagnose the nature and cause of loss of voluntary urinary bladder and bowel control (syn. incontinence), for example, in Alzheimer disease.

2 Claims, No Drawings

METHOD FOR DIAGNOSIS OF INCONTINENCE OF CORTICOCEREBRAL ORIGIN BY NEUROLOGIC EXAMINATION

FIELD OF THE INVENTION

The invention relates to methods of neurologic examination.

BACKGROUND OF THE INVENTION

The invention relates to methods of neurologic examination to diagnose incontinence, defined as loss of the function of voluntary specific control over the evacuation of the urinary bladder and the anorectum, which results from failure of cerebrocortical structures that is directly caused by the neurodegenerative process of Alzheimer disease (AD), and to distinguish incontinence, which results from failure of specific cerebrocortical structures and is caused by the neurodegenerative process of Alzheimer disease from incontinence not resulting from failure of specific cerebrocortical structures as caused by the neurodegenerative process of AD.

A methodology for diagnosis and staging of dementia by neurologic examination has previously been described in U.S. Pat. No. 5,150,716 to Franssen and Reisberg, the specification of which is incorporated herein by reference.

The methodology of the '716 patent comprises the inventors "System for Diagnosis and Staging of Dementia by Neurologic Examination", comprising 14 individual neurologic reflex measures which are the four deep tendon reflexes, the plantar response, the muscle tone, the sucking reflex (tactile), the sucking reflex (visual), the hand grasp, the foot grasp, the rooting reflex, the snout reflex, the glabella blink reflex, and the palmomental reflex, the magnitude of which is gauged on a 7-point rating scale for neurologic examination, a group of 4 neurologic reflex measures, which are the tactile sucking reflex, the hand grasp reflex, also called the palmar grasp, the foot grasp reflex, also called the plantar grasp, and the plantar response.

Permanent total incontinence in AD has been attributed to loss of cognitive abilities, such as disorientation, confusion or obliviousness to the rules of social conventions or hygiene. Incontinence in AD has also been attributed to comorbidity, that is, to secondary incidental, frequently potentially treatable and frequently transient conditions which can often be diagnosed with existing clinical procedures. Permanent incontinence in AD has also been attributed to failure of specific structures of the frontal cortex of the brain which are instrumental for the regulation of control of voluntary retainment and initiation of evacuation of the contents of the urinary bladder and the anorectum. Presumably, failure of various cortical mechanisms is caused directly by the neurodegenerative process of AD. However, no physical markers nor any other methodologies for the determination of the existence of specific regulatory brain mechanisms such as those failing in the neurodegenerative process of AD as a cause for incontinence have been claimed.

Various existing urodynamic techniques and electromyographic techniques are available to diagnose causes of incontinence in patients with or without AD. However, these techniques cannot diagnose incontinence caused by failure of specific cerebrocortical structures damaged by the neurodegenerative process of AD. In addition, these techniques generally necessitate invasive procedures such as the insertion of catheters or needles, and they often require some form of cooperation from the patient. In the advanced stages of AD, when incontinence commonly occurs, the patient is unable to cooperate.

It has been described that a permanent state of bladder and bowel incontinence, referred to as established double incontinence, inevitably occurs at a predictable point in the course of AD. As such, this state of inevitable permanent total incontinence can be considered as directly resulting from the progressive neurodegenerative process of AD.

It has been described that certain neurologic signs such as release signs (primitive reflexes) or an extensor plantar reflex are indicators of dysfunction of the cerebral cortex, in particular of the frontal cortex which also harbors the mechanisms for voluntary bladder and bowel control.

These neurologic signs have hitherto not served as indicators of incontinence associated with AD or any other cerebrocortical neurodegenerative disease process.

BRIEF DESCRIPTION OF THE PRESENT INVENTION

We therefore developed the present invention of a clinical neurologic methodology for the diagnosis of incontinence resulting from failure of specific cerebrocortical structures, caused by the neurodegenerative process of AD. The methodology is based upon a previously developed system for diagnosis and staging of dementia by neurologic examination (U.S. Pat. No. 5,150,716 Franssen and Reisberg).

Incontinence is a problem of major socioeconomic proportions. The methodology for distinguishing incontinence which is an inevitable outcome of AD, and presumably caused by the neurodegenerative process of AD, from incontinence not resulting from the neurodegenerative process of AD, and thus frequently potentially treatable, which we have discovered and which is described herein, can be of use for the development and selection of more effective treatment modalities for incontinence occurring in dementia and other diseases affecting the brain and may have a significant cost saving impact on health care.

We have discovered that particular neurologic reflexes and particular combinations of neurologic reflexes, when properly graded on a severity scale and incorporated into a diagnostic algorithm can be useful to determine the cause of permanent loss of voluntary control over the functions of storage and expulsion of the urinary bladder and the anorectum, further referred to as "incontinence". We have also discovered that reflexes can be useful to distinguish incontinence not directly resulting from the neurodegenerative process of AD from incontinence caused by loss of cerebrocortical control over the functions of storage and expulsion of the urinary bladder and the anorectum.

Our discovery is based upon the method of the application of neurologic reflexes and release signs, elicited and carefully quantified according to a previously described and patented methodology as neurologic measures for permanent incontinence resulting from the neurodegenerative process of AD.

We had previously discovered that (a) quantified neurologic reflexes and release signs are useful for the diagnosis and staging of the severity of dementia in AD; (b) specific so-called "primitive reflex" signs, collectively termed "prehensile" release signs, are indicators of severe dementia in patients with AD; (c) a specific cutaneous reflex, specifically the plantar extensor response, is an indicator of severe dementia; and (d) the previously developed methodology for diagnosis and staging of dementia referred to above can be utilized in severely demented patients who have completely lost all communicative abilities.

We have now additionally discovered that by systematically registering and quantifying the occurrence of the specific neurologic signs referred to above over the entire course of AD we can determine the presence of incontinence resulting from failure of specific cerebrocortical structures caused by the neurodegenerative process of AD.

We have also now additionally discovered that by systematically applying these specific quantified neurologic signs over the entire course of AD we can distinguish the presence of incontinence which is not directly caused by the neurodegenerative process of AD from incontinence which results from failure of specific cerebrocortical structures which is directly caused by the neurodegenerative process of AD.

It is an objective of the present invention to provide a non invasive clinical test, for diagnosis of incontinence caused by the neurodegenerative process of AD.

It is further an objective of the present invention to provide a safe and reliable clinical test for distinguishing incontinence caused by neurodegenerative process of AD from incontinence caused by factors other than the neurodegenerative process of AD.

It is further an objective of the present invention to provide a safe and reliable clinical test for diagnosis of incontinence caused by the neurodegenerative process of AD, which is independent of the patient's cognitive status.

It is further an objective of the present invention to provide a safe and reliable physical marker of the course and progression of the neurodegenerative process of AD.

DETAILED DESCRIPTION OF A PREFERRED EMBODIMENT

In accordance with the present invention, measures were derived from the system for Diagnosis and Staging of Dementia by neurologic Examination (U.S. Pat. No. 5,150,716) and used to assess healthy elderly individuals, elderly subjects with mild cognitive and functional impairment and patients with dementia of the Alzheimer type in all stages of clinical severity. Specific scoring methodologies, previously developed and described by the inventors (U.S. Pat. No. 5,150,716) were used to rate degree of neurologic reflex, release sign and muscle tone magnitude obtained on these measures.

Specifically, these measures described in the previous patent included deep tendon reflexes (syn. muscle stretch reflexes), namely the biceps reflexes, triceps reflexes, quadriceps reflexes, and gastrocnemius-soleus reflexes (syn. triceps surae reflexes); prehensile release signs, namely the tactile sucking reflex, visual sucking reflex, hand grasp reflex, foot grasp reflex, and rooting reflex; nociceptive release signs, namely the snout reflex, glabellar blink reflex and the palmomental reflex; the plantar response (extensor plantar reflex); and muscle tone (paratonia).

In accord with the present invention, one new neurologic examination measure or summary reflex measure was developed, consisting of a combination of the tactile sucking reflex, the hand grasp reflex (syn. palmar grasping), the foot grasp reflex (synplantar grasping), and the plantar extensor reflex (syn. Babinski sign). The scoring methodology used consisted of the 7-point rating scale for neurologic examination as described in the System for Diagnosis and Staging of Dementia by Neurologic Examination (U.S. Pat. No. 5,150,716).

For the three prehensile release signs employed, (i.e., the tactile sucking reflex, the hand grasp reflex, and the foot grasp reflex, as well as for the plantar extensor reflex, a score of equal to or greater than 5 on the 7-point rating scale for neurologic examination as described in the System for Diagnosis and Staging of Dementia by Neurologic Examination (U.S. Pat. No. 5,150,716), indicated a positive reflex.

When the reflex consisted of a bilaterally elicited measure as is the case in the hand grasp reflex, the foot grasp reflex and the plantar extensor reflex, the higher score is employed and is indicative of a positive reflex. Hence if either the right and/or left reflex is 5 or greater, a positive reflex response is scored.

Specifically, for the tactile sucking reflex, a score of 5 or greater is defined as: lips of the patient grasp eliciting stimulus followed by distinct sucking movements within 15 seconds of gentle stroking of the lips of the patient. A score of 5 or greater indicates a positive reflex.

For the hand grasp reflex, a score of 5 or greater is defined as: a distinct grasping with the hand by the patient of the eliciting tactile stimulus, applied for 15 seconds or less, to the palm of the hand of the patient. A score of 5 or greater on the right or left side indicates a positive reflex.

For the foot grasp reflex, a score of 5 or greater is defined as: a distinct tonic plantar flexion of the toes of the foot of the patient in response to a tactile stimulus applied for 15 seconds or less to the anterior part of the sole of the foot of the patient. A score of 5 or greater on the right or left side indicates a positive reflex.

For the extensor plantar reflex, a score of 5 or greater is defined as a tonic dorsiflexion of the great toe of the foot of the patient in response to a tactile moving stimulus to the lateral aspect of the sole of the foot applied for 15 seconds or less. A score of 5 or greater on the right or left side indicates a positive reflex.

For the summary measure, a score of 5 or greater is defined as a score of 5 or greater on either the tactile sucking reflex, the hand grasp, the foot grasp reflex or the plantar extensor reflex, as defined above.

The inventors have discovered that the present invention can be employed to discover the presence of incontinence in AD which is caused by the neurodegenerative process of AD.

When 360 continent AD patients were compared to 61 permanently totally incontinent AD patients, 11 continent AD patients (3.0%) had a positive tactile sucking reflex, as compared to 46 permanently totally incontinent AD patients (75.4%). The difference in prevalence of a positive tactile sucking reflex between the two patient groups was highly significant (p<0.001). Consequently, this measure is useful as a physical marker of permanent total incontinence associated with AD.

When 360 continent AD patients were compared to 61 permanently totally incontinent AD patients, 9 continent AD patients had a positive hand grasp reflex (2.5%), as compared to 45 permanently totally incontinent AD patients (73.7%). The difference in prevalence of a positive hand grasp reflex between the two groups of patients was highly significant (p<0.001). Consequently, this measure is useful as a physical marker of permanent total incontinence of AD.

When 360 continent AD patients were compared to 61 permanently totally incontinent AD patients, none of the continent AD patients had a positive foot grasp reflex, as compared to 23 permanently totally incontinent patients (37.7%). The difference in prevalence of a positive foot grasp reflex between the two groups of patients was highly significant (p<0.001). Consequently, this measure is useful as a physical marker of permanent total incontinence of AD.

When 360 continent AD patients were compared to 61 permanently totally incontinent AD patients, 9 continent patients had a positive plantar extensor reflex (2.5%), as compared to 30 permanently totally incontinent AD patients (49.2%). The difference in prevalence of a positive plantar extensor reflex between the two groups of patients was highly significant (p<0.001). Consequently, this measure is useful as a physical marker of permanent total incontinence of AD.

When 360 continent AD patients were compared to 61 permanently totally incontinent AD patients, 27 continent patients had a positive score on the summary measure (7.5%), consisting of a positive tactile sucking reflex, hand grasp reflex (right or left), foot grasp reflex (right or left) or plantar extensor reflex (right or left) as compared to 56 permanently totally incontinent patients (91.8%). The difference in prevalence of a positive score on the summary measure between the two groups of patients was highly significant (p<0.001). Consequently, this measure is useful as a physical marker of permanent total incontinence of AD.

The inventors have discovered that the present invention presents a reliable and safe clinical test for the diagnosis of inevitable permanent incontinence of AD.

When ambulant continent AD patients who were deficient in activities of daily living were compared with ambulant AD patients who were permanently incontinent, the specificity of the summary measure in differentiating continent from incontinent patients was 85.8%, the sensitivity was 86.2% and the overall accuracy was 85.9% (chi squares= 55.8, p<0.001). Consequently this measure is a specific, sensitive and accurate marker of permanent incontinence resulting from the neurodegenerative process of AD.

Clinical Advantages of the Assessment Procedures

This invention has accomplished the following:
1. It provides a simple and safe cognition-independent method for diagnosing inevitable incontinence associated with failure or disconnection of cortical regulatory mechanisms which specifically effectuate voluntary control of urinary bladder and anorectum.
2. It provides a simple and safe instrument for distinguishing incontinence caused by failure of specific cortical regulatory mechanisms for effectuation of bladder and bowel regulation from incontinence caused by factors not directly associated with failure of cortical regulatory mechanisms specifically controlling voluntary regulation of the contents of urinary bladder and anorectum.
3. It provides a process for evaluating for the presence of brain dysfunction which is specifically related to the occurrence of incontinence.
4. It provides a physical marker for progressive incontinence secondary to failure or disconnection of cortical regulatory mechanisms in neurodegenerative disease.
5. It provides a physical marker of the course of Alzheimer disease.
6. It provides a mechanism for a more effective approach to the treatment of incontinence.

We claim:

1. The method for diagnosing incontinence resulting from failure of cortical regulating mechanisms for voluntary control of discharge of urinary bladder and anorectum, and for distinguishing incontinence resulting from failure of cortical regulatory control mechanisms from incontinence caused by mechanisms other than failure of regulatory cortical mechanisms comprising:

(a) selecting from a system for diagnosis and staging of dementia by neurologic examination 14 individual reflexes which are the 4 deep tendon reflexes, the plantar response, the muscle tone, the tactile sucking reflex, the visual sucking reflex, the hand grasp, the foot grasp, the rooting reflex, the snout reflex, the glabella blink reflex, and the palmomental reflex, the magnitude of which is gauged on a 7-point rating scale for neurologic examination, a group of 4 neurologic reflex measures, which are the tactile sucking reflex, the hand grasp reflex, also called the palmar grasp, the foot grasp reflex, also called the plantar grasp, and the plantar response for the purpose of diagnosing incontinence directly caused by failing regulatory cortical control mechanisms for the urinary bladder and anorectum resulting from neurodegenerative process;

(b) determining the presence of said 4 reflexes which are the tactile sucking reflex, the hand grasp reflex, also called the palmar grasp, the foot grasp reflex, also called the plantar grasp, and the plantar response as a defined magnitude of activity as measured on said 7-point rating scale for neurologic examination that is a score of equal to or greater than 5;

(c) developing a new neurologic measurement from a specific combination of individual quantified reflex measurements comprising a combination of said 4 neurologic reflex measures; and, (d) using said quantified individual neurologic reflex measurements and said combination of neurologic quantified measurement of a defined magnitude of activity as measured on said rating scale for neurologic examination to determine presence of incontinence directly caused by failure of regulating cortical mechanisms for the urinary bladder and anorectum resulting from the neurodegenerative process.

2. The method of claim 1 wherein said step (d) of using said measurements for the purpose of diagnosing incontinence caused by the failure of cortical control mechanisms as a result of a neuro-degenerative process comprises the selection of said set of neurologic reflex and related measures comprising the tactile sucking reflex, the hand grasp reflex, the foot grasp reflex and the plantar response at a magnitude equal to or greater than 5 on said 7-point rating scale.

\* \* \* \* \*